US011547383B2

(12) United States Patent
Lee et al.

(10) Patent No.: US 11,547,383 B2
(45) Date of Patent: Jan. 10, 2023

(54) ULTRASOUND IMAGING APPARATUS AND METHOD OF GENERATING ULTRASOUND IMAGE

(71) Applicants: SAMSUNG MEDISON CO., LTD., Hongcheon-gun (KR); Korea University Research and Business Foundation, Seoul (KR)

(72) Inventors: Dongeun Lee, Seongnam-si (KR); Jinyong Lee, Seongnam-si (KR); Minjeong Oh, Seoul (KR); Geumjoon Cho, Seoul (KR); Hyejin Choi, Seoul (KR)

(73) Assignees: SAMSUNG MEDISON CO., LTD., Hongcheon-gun (KR); Korea University Research and Business Foundation, Seoul (KR)

( * ) Notice: Subject to any disclaimer, the term of this patent is extended or adjusted under 35 U.S.C. 154(b) by 610 days.

(21) Appl. No.: 16/548,115

(22) Filed: Aug. 22, 2019

(65) Prior Publication Data

US 2020/0237338 A1 Jul. 30, 2020

(30) Foreign Application Priority Data

Jan. 30, 2019 (KR) .................. 10-2019-0011983

(51) Int. Cl.
*A61B 8/08* (2006.01)
*A61B 8/00* (2006.01)
*A61B 8/14* (2006.01)

(52) U.S. Cl.
CPC .............. *A61B 8/0866* (2013.01); *A61B 8/14* (2013.01); *A61B 8/463* (2013.01); *A61B 8/5246* (2013.01)

(58) Field of Classification Search
CPC ......... A61B 8/14; A61B 8/0866; A61B 8/463; A61B 8/5246; A61B 8/5223; A61B 8/461; A61B 8/467
See application file for complete search history.

(56) References Cited

U.S. PATENT DOCUMENTS

| 10,743,844 B2 | 8/2020 | Ardon et al. |
| 2016/0045152 A1 | 2/2016 | Singhal et al. |
| 2017/0206659 A1 | 7/2017 | Perrey et al. |

FOREIGN PATENT DOCUMENTS

| JP | 2006-167100 A | 6/2006 |
| JP | 2015-171476 A | 10/2015 |

(Continued)

OTHER PUBLICATIONS

Communication dated Jan. 31, 2020, issued by the European Patent Office in counterpart European Patent Application No. 19183319.3.

(Continued)

*Primary Examiner* — Boniface Ngathi N
(74) *Attorney, Agent, or Firm* — Sughrue Mion, PLLC

(57) ABSTRACT

Provided are an ultrasound imaging apparatus and a method of generating an ultrasound image. The method includes: transmitting ultrasound signals to an object; receiving ultrasound echo signals from the object; generating ultrasound image data based on the received ultrasound echo signals; identifying a fetus's skull from the ultrasound image data; identifying, based on the identified fetus's skull, a caput succedaneum region corresponding to caput succedaneum occurring in the fetus; and displaying information about the caput succedaneum region.

20 Claims, 14 Drawing Sheets

(56) References Cited

FOREIGN PATENT DOCUMENTS

| JP | 2016-140588 A | 8/2016 | |
|---|---|---|---|
| JP | 2017-525445 A | 9/2017 | |
| KR | 10-2011-0064101 A | 6/2011 | |
| KR | 10-1077752 B1 | 10/2011 | |
| KR | 10-2016-0049139 A | 5/2016 | |
| WO | 2016/040024 A1 | 3/2016 | |
| WO | 2016/190256 A1 | 12/2016 | |
| WO | WO-2016190256 A1 * | 12/2016 | ............... A61B 8/14 |

OTHER PUBLICATIONS

Eggebo, et al., "A model to predict vaginal delivery in nulliparous women based on maternal characteristics and intrapartum ultrasound", Sep. 2015, 6 pages total, American Journal of Obstetrics & Gynecology.

Mnon Gilboa et al., "Caput succedaneum thickness in prolonged second stage of labour: a clinical evaluation", Australian and New Zealand Journal of Obstetrics and Gynaecology, vol. 53, May 7, 2013, pp. 459-463.

Wassim A. Hassan et al., "Intrapartum assessment of caput succedaneum by transperineal ultrasound: a two-centre pilot study," Australian and New Zealand Journal of Obstetrics and Gynaecology, vol. 55, Mar. 15, 2015, pp. 401-403.

T. Ghi et al., "ISUOG Practice Guidelines: intrapartum ultrasound", Ultrasound Obstet Gynecol 2018; Jul. 4, 2018, vol. 52: pp. 128-139.

\* cited by examiner

ULTRASOUND IMAGING APPARATUS AND METHOD OF GENERATING ULTRASOUND IMAGE

CROSS-REFERENCE TO RELATED APPLICATION(S)

This application is based on and claims priority under 35 U.S.C. § 119 to Korean Patent Application No. 10-2019-0011983, filed on Jan. 30, 2019, in the Korean Intellectual Property Office, the disclosure of which is incorporated by reference herein in its entirety.

BACKGROUND

1. Field

The disclosure relates to ultrasound imaging apparatuses and methods of generating an ultrasound image by using an ultrasound imaging apparatus.

2. Description of Related Art

Ultrasound imaging apparatuses transmit ultrasound signals generated by transducers of a probe to an object and detect information about signals reflected from the object, thereby obtaining at least one image of an internal part, for example, soft tissue or blood flow, of the object.

Ultrasound imaging apparatuses are compact, affordable, and display images in real time. Furthermore, as they are very safe due to lack of radiation exposure, such ultrasound imaging apparatuses have been widely used together with other types of diagnostic imaging apparatuses such as an X-ray diagnostic apparatus, a computed tomography (CT) scanner, a magnetic resonance imaging (MRI) apparatus, a nuclear medicine diagnostic apparatus, etc.

Ultrasound imaging apparatuses are used to check the status of a fetus, such as a fetal size, growth rate, and normal development from an early stage of pregnancy until delivery of the fetus. Furthermore, ultrasound imaging apparatuses are used to check fetal conditions and the position of the skull of a fetus. For example, an ultrasound imaging apparatus may be used to identify caput succedaneum in a fetus.

Referring to FIGS. 11, 12A, and 12B, when a fetus 15 is delivered from a mother's body 11, pressure is exerted on a skull 16 of the fetus 15 as the fetus 15 passes through a birth canal 12. The pressure on the skull 16 of the fetus 15 may cause edema between the skull 16 and a scalp 18 of the fetus 15. Caput succedaneum 17 refers to the edema that occurs between the skull 16 and the scalp 18.

The longer it takes for the fetus 15 to pass through the birth canal 12, the greater the pain that the mother and the fetus 15 suffer, which may endanger their lives. Thus, a doctor needs to prepare for labor by accurately identifying a position of the skull 16 of the fetus 15. However, the doctor is likely to misidentify the caput succedaneum 17 as the skull 16 of the fetus 15. In other words, the doctor may fail to accurately determine the progress of the labor by misidentifying the caput succedaneum 17 as the skull 16. The doctor may also fail to accurately determine whether the fetus 15 is able to easily pass through the birth canal 12.

Furthermore, as the skull 16 of the fetus 15 passes through the birth canal 12, the caput succedaneum 17 may occur to a greater extent. Thus, the doctor may determine whether the fetus 15 is able to easily pass through the birth canal 12 based on a size of the caput succedaneum 17.

Thus, there is a need for an ultrasound imaging apparatus capable of accurately acquiring information about a position of the skull 16 of the fetus 15 and a size of the caput succedaneum 17.

SUMMARY

Provided are ultrasound imaging apparatuses and methods of generating an ultrasound image, which are capable of identifying and measuring caput succedaneum that may occur in a fetus during a delivery procedure.

Additional aspects will be set forth in part in the description which follows and, in part, will be apparent from the description, or may be learned by practice of the presented embodiments.

In accordance with an aspect of the disclosure, a method of generating an ultrasound image, performed by an ultrasound imaging apparatus, includes: transmitting ultrasound signals to an object; receiving ultrasound echo signals from the object; generating ultrasound image data based on the received ultrasound echo signals; identifying a fetus's skull from the ultrasound image data; identifying, based on the identified fetus's skull, a caput succedaneum region corresponding to caput succedaneum occurring in the fetus; and displaying information about the caput succedaneum region.

In accordance with another aspect of the disclosure, an ultrasound imaging apparatus includes: an ultrasound probe configured to transmit ultrasound signals to an object and receive ultrasound echo signals from the object; a processor configured to generate ultrasound image data based on the received ultrasound echo signals, identify a fetus's skull from the ultrasound image data, and identify, based on the identified fetus's skull, a caput succedaneum region corresponding to caput succedaneum occurring in the fetus; and a display displaying information about the caput succedaneum region.

In accordance with another aspect of the disclosure, a computer program product includes a computer-readable recording medium having recorded thereon instructions executable on a computer to cause an ultrasound imaging apparatus to perform the method of generating an ultrasound image.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
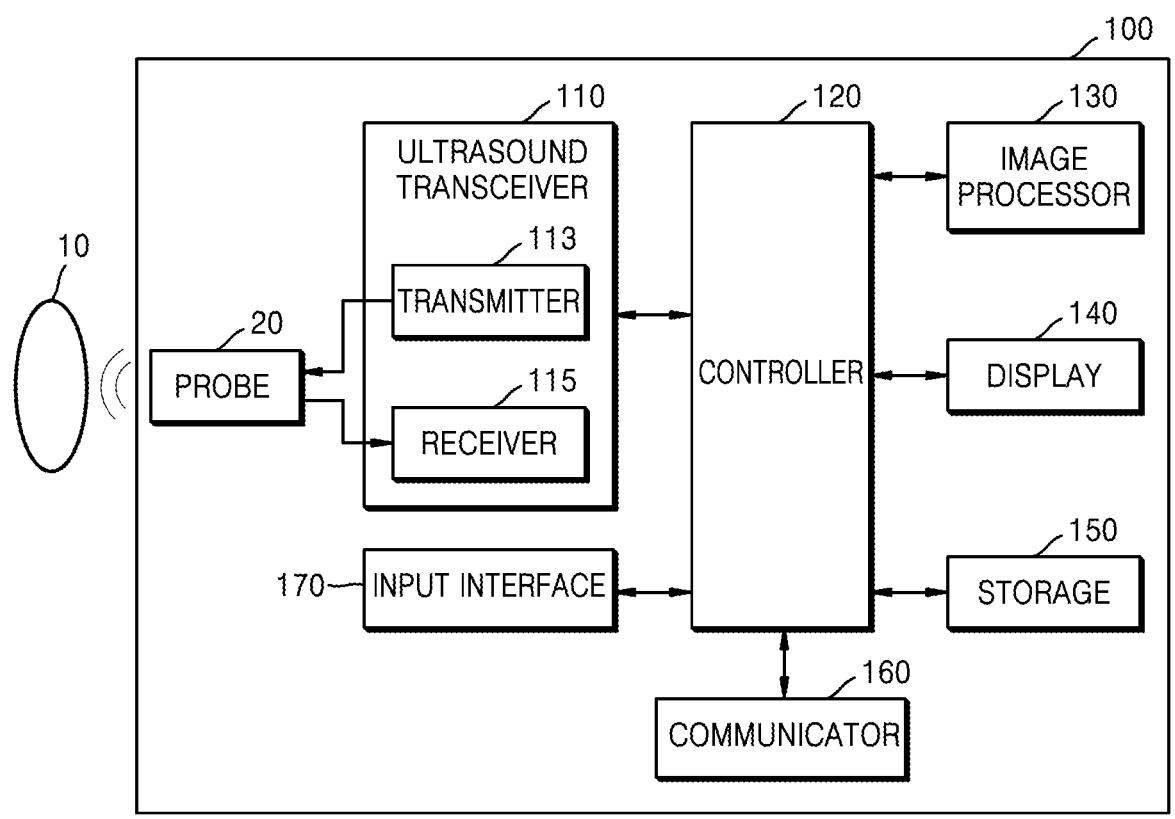
FIG. 1 is a block diagram illustrating an ultrasound imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements. Expressions such as "at least one of," when preceding a list of elements, modify the entire list of elements and do not modify the individual elements of the list In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom. As another example, the object may include at least a part of a mother's body having a fetus therein.

Throughout the specification, an ultrasound image refers to an image of an object processed based on ultrasound signals transmitted to the object and reflected therefrom.

Hereinafter, embodiments of the disclosure will be described in detail with reference to the accompanying drawings.

FIG. 1 is a block diagram illustrating a configuration of an ultrasound imaging apparatus 100, i.e., a diagnostic apparatus, according to an exemplary embodiment.

Referring to FIG. 1, the ultrasound imaging apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound imaging apparatus 100 may be of a cart-type or a portable-type ultrasound imaging apparatus, which is portable, moveable, mobile, or hand-held. Examples of the portable-type ultrasound imaging apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound imaging apparatus 100 may be formed in one body (e.g., disposed in a single housing), or the probe 20 and the ultrasound imaging apparatus 100 may be formed separately (e.g., disposed separately in separate housings) but linked wirelessly or via wires. In addition, the ultrasound imaging apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers. The controller 120 may include the image processor 130.

The image processor 130 may generate an ultrasound image by using ultrasound data generated from the ultrasound receiver 115.

The display 140 may display a generated ultrasound image and various pieces of information processed by the ultrasound imaging apparatus 100. The ultrasound imaging apparatus 100 may include two or more displays 140 according to the present exemplary embodiment. The display 140 may include a touch screen in combination with a touch panel.

The controller 120 may control the operations of the ultrasound imaging apparatus 100 and flow of signals between the internal elements of the ultrasound imaging apparatus 100. The controller 120 may include a memory for storing a program or data to perform functions of the ultrasound imaging apparatus 100 and at least one of processor and/or at least one of microprocessor (not shown) for processing the program or data.

A processor may include a general-purpose processor such as a central processing unit (CPU) or a special-purpose processor manufactured for generating an ultrasound image.

At least one processor may operate as the image processor 130. In other words, the processor may generate an ultrasound image based on ultrasound data. Furthermore, the processor may identify a predetermined region in the ultrasound image and measure at least one of a thickness, an area, and a volume of the predetermined region. The processor may also acquire additional information about the predetermined region. The processor may execute an instruction or application for acquiring additional information that is used to facilitate a diagnosis by a user.

For example, the controller 120 may control the operation of the ultrasound imaging apparatus 100 by receiving a control signal from the input interface 170 or an external apparatus.

The ultrasound imaging apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound imaging apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound imaging apparatus 100 may process the data of the external apparatus in response to the control signal of the controller 120 received via the communicator 160.

A program for controlling the ultrasound imaging apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound imaging apparatus 100, input and/or output ultrasound data, ultrasound images, applications, etc. The storage 150 may include a transitory memory (e.g., random access memory (RAM), a buffer, etc.) or a non-transitory memory (e.g., a data storage such as a magnetic disc).

The input interface 170 may receive a user's input to control the ultrasound imaging apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound imaging apparatus 100 according to the present exemplary embodiment is described below with reference to FIGS. 2A, 2B, and 2C.

Figure 2A:
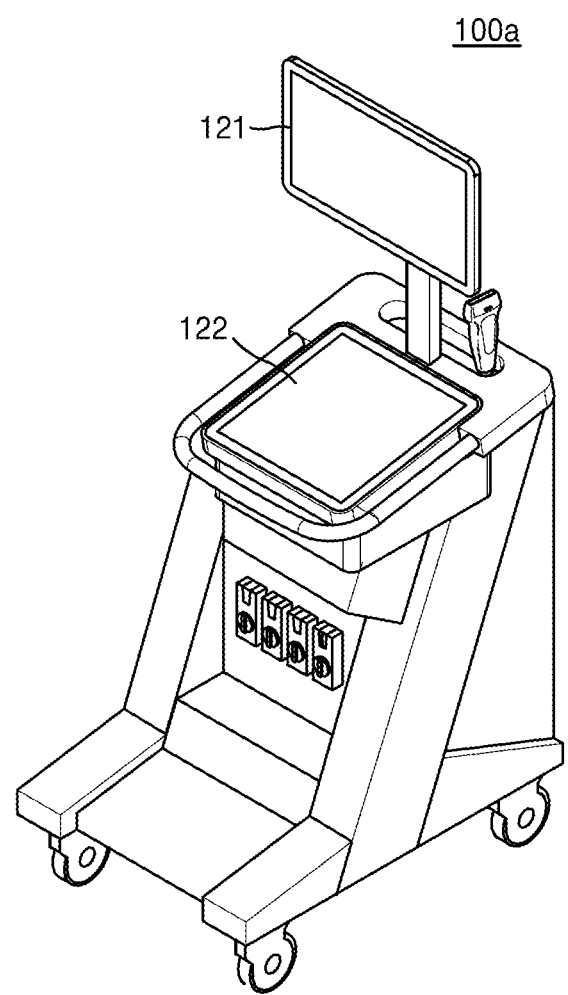
FIGS. 2A, 2B, and 2C are diagrams respectively illustrating an ultrasound imaging apparatus according to an exemplary embodiment.
Figure 2B:
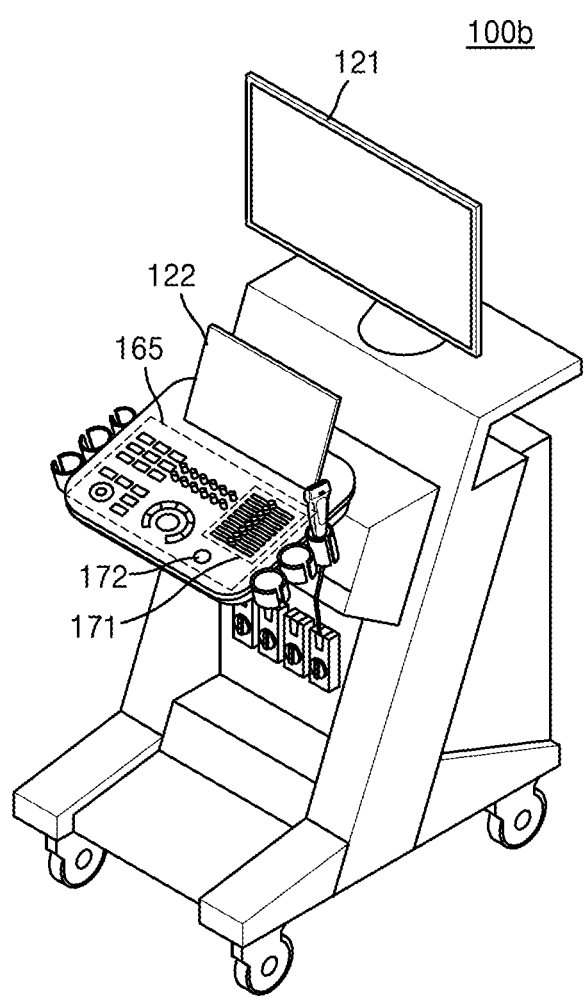
Figure 2C:
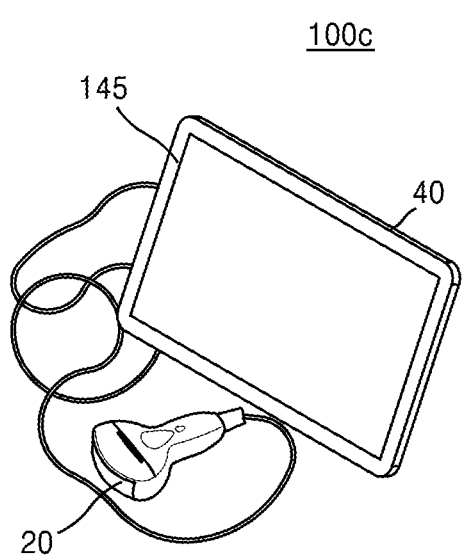

FIGS. 2A, 2B, and 2C are diagrams illustrating ultrasound imaging apparatus according to an exemplary embodiment.

Referring to FIGS. 2A and 2B, the ultrasound imaging apparatus 100 may include a main display 121 and a sub-display 122. At least one among the main display 121 and the sub-display 122 may include a touch screen. The main display 121 and the sub-display 122 may display ultrasound images and/or various pieces of information processed by the ultrasound imaging apparatus 100. The main display 121 and the sub-display 122 may provide graphical user interfaces (GUI), thereby receiving user's inputs of data to control the ultrasound imaging apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound imaging apparatus 100 may control the display of the ultrasound image on the main display 121 by using the input control data.

Referring to FIG. 2B, the ultrasound imaging apparatus 100 may include a control panel 165. The control panel 165 may include buttons, trackballs, jog switches, or knobs, and may receive data to control the ultrasound imaging apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound imaging apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound imaging apparatus 100 may include a portable device. An example of the portable ultrasound imaging apparatus may include smart phones including probes and applications, laptop computers, personal digital assistants (PDAs), or tablet PCs, but an exemplary embodiment is not limited thereto.

The ultrasound imaging apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound imaging apparatus 100, and a GUI.

Figure 3:
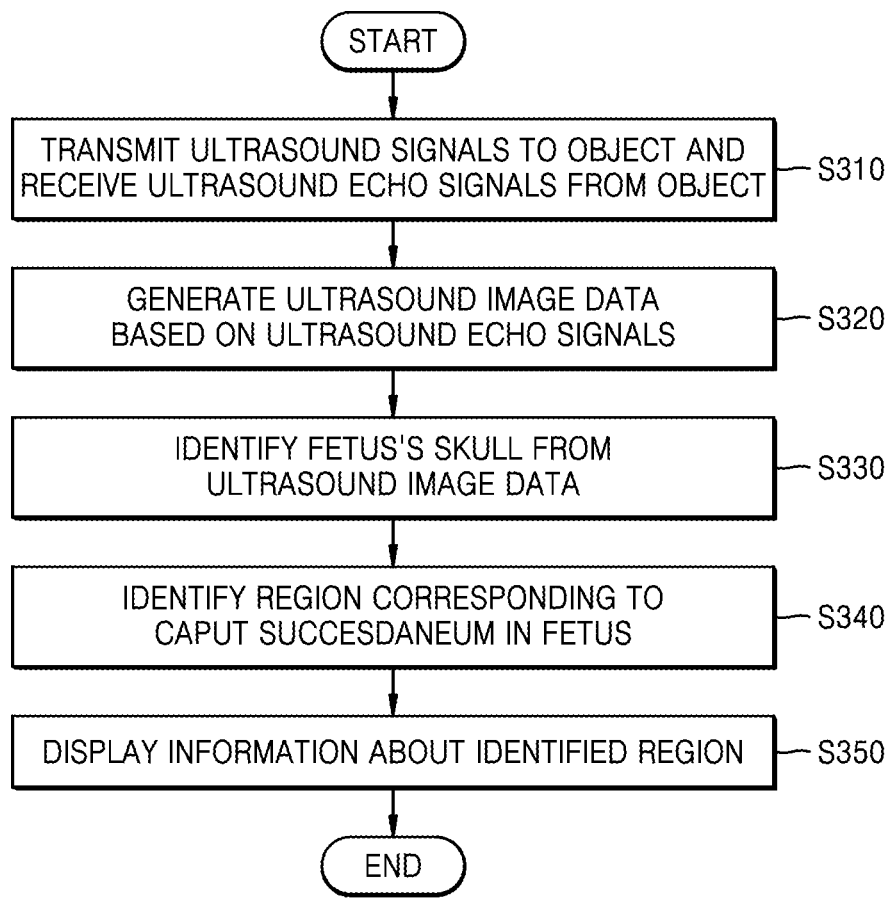
FIG. 3 is a flowchart of a method of generating an ultrasound image, performed by an ultrasound imaging apparatus, according to an embodiment.

FIG. 3 is a flowchart of a method, performed by the ultrasound imaging apparatus 100, of generating an ultrasound image, according to an embodiment.

Referring to FIG. 3, the ultrasound imaging apparatus 100 may identify an area corresponding to caput succedaneum that occurs in a fetus and display information about the identified area.

Caput succedaneum refers to edema that occurs in soft tissue of a presenting part of a fetus's skull due to a pressure inside a mother's birth canal when the fetus is delivered from the mother's body.

By misidentifying the caput succedaneum as the fetus's skull, the user may fail to select an appropriate labor method. Thus, the user needs to identify the caput succedaneum in an ultrasound image and obtain information about the caput succedaneum.

The information about the caput succedaneum may include information about a position of a caput succedaneum region in an ultrasound image, information about an outline of the caput succedaneum region, information about a thickness, an area, and a volume of the caput succedaneum region and information about the risk of labor obtained based on at least one of the thickness, area, and volume of the caput succedaneum region.

The probe 20 of the ultrasound imaging apparatus 100 may transmit ultrasound signals to the object 10 and receive ultrasound echo signals from the object 10 (operation S310). For example, when the probe 20 is a convex ultrasound probe, the probe 20 may transmit ultrasound signals with frequencies of 3 to 5 MHz to the object 10. The probe 20 may receive ultrasound echo signals generated by reflecting the ultrasound signals from the object 10.

The processor of the ultrasound imaging apparatus 100 may generate ultrasound image data based on the received ultrasound echo signals (operation S320).

According to an embodiment, the ultrasound image data may include at least one of data for generating a two-dimensional (2D) ultrasound image and data for generating a three-dimensional (3D) ultrasound image. Furthermore, the ultrasound image data may include data for generating a plurality of ultrasound cross-sectional images.

According to an embodiment, the ultrasound image data may include image data with respect to a fetus's skull, caput succedaneum that occurs in the fetus, and at least one mother's anatomical structure (e.g., a pubis).

The processor of the ultrasound imaging apparatus 100 may identify a fetus's skull from the ultrasound image data (operation S330).

According to an embodiment, the processor may identify the fetus's skull from pieces of the ultrasound image data respectively corresponding to a plurality of ultrasound cross-sectional images.

According to an embodiment, the processor may identify the fetus's skull by identifying a region that is composed of pixels having high brightness values in the ultrasound image data and corresponds to a part of an ellipse. The processor may identify the fetus's skull by using various algorithms known in the art with respect to a method of identifying a fetus's skull in an ultrasound image.

The processor of the ultrasound imaging apparatus 100 may identify, based on the identified fetus's skull, a caput succedaneum region corresponding to a caput succedaneum in the fetus (operation S340).

The processor may identify, based on ultrasound image data, a caput succedaneum region corresponding to a caput succedaneum in the fetus.

According to an embodiment, the processor may identify, as a caput succedaneum region, pixels having lower brightness values than their neighboring pixels from among a plurality of pixels located along a direction of a normal line to the fetus's skull identified in operation S330.

According to an embodiment, the processor may identify a fetus's scalp around the skull identified in operation S330 and then identify a region between the skull and the scalp as a caput succedaneum region.

According to an embodiment, the processor may identify a caput succedaneum region in an ultrasound cross-sectional image showing a largest skull from among a plurality of ultrasound cross-sectional images, as described in more detail below with reference to FIG. 4.

According to an embodiment, the processor may measure a thickness of the identified caput succedaneum region. The processor may measure a thickness of a caput succedaneum region in each of a plurality of ultrasound cross-sectional images. The processor may measure a thickness of a caput succedaneum region in an ultrasound cross-sectional image showing a largest skull from among a plurality of ultrasound cross-sectional images, as described in more detail below with reference to FIG. 5.

According to an embodiment, the processor may measure an area of the identified caput succedaneum region. The processor may respectively measure areas of caput succedaneum regions in a plurality of ultrasound cross-sectional images. The processor may compare widths of the measured areas of the caput succedaneum regions with one another.

The processor may measure an area of a caput succedaneum region in an ultrasound cross-sectional image showing a largest skull from among a plurality of ultrasound cross-sectional images, as described in more detail below with reference to FIG. 6.

According to an embodiment, the processor may calculate a volume of the identified caput succedaneum region. The processor may obtain a volume of a caput succedaneum region by respectively measuring areas of caput succedaneum regions in a plurality of ultrasound cross-sectional images and stacking the measured areas of the caput succedaneum regions together, as described in more detail below with reference to FIG. 6.

According to an embodiment, the processor may identify a shaded region included in an ultrasound image.

A shaded region may include at least a part of a caput succedaneum region. The processor may identify a part of a caput succedaneum region excluding the shaded region. The processor may identify an outline, a thickness, and an area of the part of the caput succedaneum region excluding the shaded region, as described in more detail below with reference to FIGS. 7 and 8.

The processor may estimate a caput succedaneum region included in a shaded region. The processor may also estimate an outline, a thickness, and an area of the caput succedaneum region based on a result of the estimating, as described in more detail below with reference to FIGS. 7 and 9.

According to an embodiment, the input interface 170 of the ultrasound imaging apparatus 100 may receive a user input with respect to a caput succedaneum region. For example, the input interface 170 may receive a user input for setting an outline of the caput succedaneum region. As another example, the input interface 170 may receive a user input for adjusting an outline of the caput succedaneum region. The processor may control the display 140 to display an interface for receiving a user input with respect to the caput succedaneum region.

The processor may identify a caput succedaneum region based on a user input. For example, the processor may identify a caput succedaneum region based on a user input for setting an outline of the caput succedaneum region. As another example, the processor may identify a caput succedaneum region based on a user input for adjusting an outline of the caput succedaneum region.

The display 140 of the ultrasound imaging apparatus 100 may display information about the caput succedaneum region (operation S350). The information about the caput succedaneum region refers to a series of pieces of information related to a caput succedaneum occurring in the fetus. For example, the information about the caput succedaneum region may include, but is not limited to, pieces of information about an outline, an area, and a volume of the caput succedaneum region and information about the risk of labor due to the caput succedaneum region. In other words, the information about the caput succedaneum region may further include information such as a ratio of an area of the caput succedaneum region to an area of the skull and a ratio of a volume of the caput succedaneum region to a volume of the skull.

The processor may control the display 140 to display the information about the caput succedaneum region in at least a part of an ultrasound image.

For example, the processor may control the display 140 to overlay a line representing an outline of the caput succedaneum region onto the caput succedaneum region in the ultrasound image.

As another example, the processor may color-code the caput succedaneum region as a certain color and control the display 140 to display the color-coded caput succedaneum region. In detail, the processor may color-code the caput succedaneum region with a color corresponding to the risk of labor in a pregnant woman. The display 140 may display the color-coded caput succedaneum region, as described in more detail below with reference to FIG. 10.

As another example, the processor may control the display 140 to overlay onto the ultrasound image a marker representing a position where a thickness of the caput succedaneum region is measured.

As another example, the processor may control the display 140 to display information related to at least one of measured thickness, area, and volume of the caput succedaneum region in at least a part of the ultrasound image.

Figure 4:
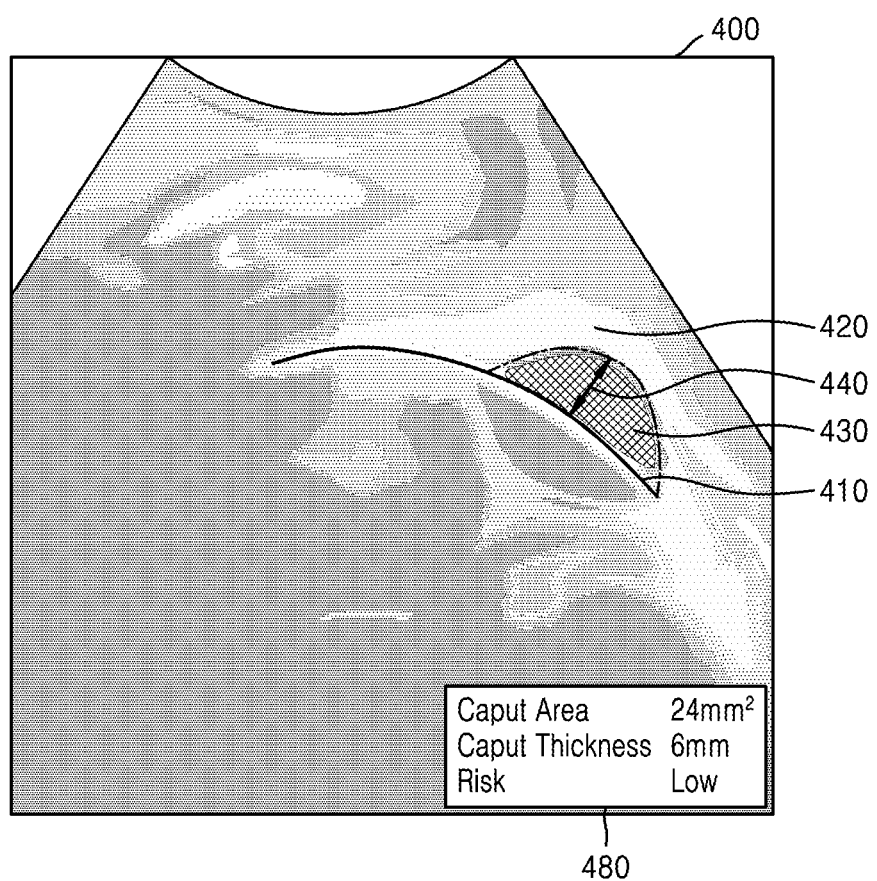
FIG. 4 is an example in which an ultrasound imaging apparatus displays information about caput succedaneum that occurs in a fetus, according to an embodiment.

FIG. 4 is an example in which the ultrasound imaging apparatus 100 displays information about caput succedaneum that occurs in a fetus, according to an embodiment.

The ultrasound imaging apparatus 100 may receive ultrasound echo signals from the object 10 via the probe 20. The ultrasound imaging apparatus 100 may acquire ultrasound image data based on the ultrasound echo signals. The ultrasound image data may include 2D ultrasound image data and 3D ultrasound image data. The ultrasound image data may include pieces of data respectively corresponding to a plurality of ultrasound cross-sectional images. The ultrasound image data may include ultrasound image data with respect to a fetus's skull, a caput succedaneum, and a mother's anatomical structure.

Referring to FIG. 4, the processor of the ultrasound imaging apparatus may acquire ultrasound image data including an ultrasound image 400 showing a fetus's skull, a scalp, a caput succedaneum, and a mother's pubis. The mother's pubis may be used for determining the fetus's skull. The mother's pubis may also be used for selecting a reference cross-section from among a plurality of ultrasound cross-sectional images.

According to an embodiment, the processor may identify a first region 410 corresponding to the fetus's skull from the ultrasound image data. For example, the processor may identify the fetus's skull by identifying a region that is composed of pixels having high brightness values in the ultrasound image data and corresponds to a part of an ellipse.

According to an embodiment, the processor may identify a caput succedaneum region from among a plurality of pixels located along a direction of a normal line to the identified fetus's skull.

For example, the processor may identify, from the plurality of pixels located along the direction of the normal line to the skull, a second region 420 corresponding to a fetus's scalp and a caput succedaneum region 430 corresponding to a caput succedaneum occurring in the fetus.

In detail, the processor may identify, as the second region 420, a region composed of pixels having similar brightness values to the pixels in the first region 410 from among the plurality of pixels located along the direction of the normal line to the skull. The processor may also identify a region corresponding to a curve including an ellipse located in the vicinity of the first region 410.

The processor may identify, as the caput succedaneum region 430, pixels that are located between the first and second regions 410 and 420 and have lower brightness values than those in the first and second regions 410 and 420. A caput succedaneum refers to swelling or edema caused by a pressure exerted on a fetal head as the fetus passes through a mother's birth canal. A caput succedaneum region in an ultrasound image is represented as lower brightness values than regions corresponding to a fetal skull and a fetal scalp. Thus, the processor may identify a region that is located near the first region 410 and has low brightness values as the caput succedaneum region 430.

The ultrasound imaging apparatus 100 may display information about the caput succedaneum region 430.

According to an embodiment, the ultrasound imaging apparatus 100 may show an outline of the caput succedaneum region 430 as a line. In other words, the processor may control the display 140 to overlay a line of a predetermined color (e.g., white, yellow, or red) onto the outline of the caput succedaneum region 430.

According to an embodiment, the ultrasound imaging apparatus 100 may color-code the caput succedaneum region 430 and display the color-coded caput succedaneum region 430. The processor may color-code the inside of the caput succedaneum region 430 with a predetermined color (e.g., green, yellow, blue, or red) and control the display 140 to display the color-coded caput succedaneum region 430, thereby allowing the user to easily recognize the color-coded caput succedaneum region 430.

According to an embodiment, the ultrasound imaging apparatus 100 may color-code the caput succedaneum region 430 with a color corresponding to the risk of labor and display the color-coded caput succedaneum region 430, as described in more detail below with reference to FIG. 10.

According to an embodiment, the processor may measure a thickness and an area of the caput succedaneum region 430. The processor may control the display 140 to display a marker 440 indicating a region where the thickness of the caput succedaneum region 430 is measured. The processor may also control the display 140 to display information 480 about the measured thickness and area of the caput succedaneum region 430.

According to an embodiment, the processor may calculate a volume of the caput succedaneum region 430. The processor may control the display 140 to display information about the volume of the caput succedaneum region 430.

According to the disclosure, the user may easily recognize the caput succedaneum region 430, and thus may not misidentify the caput succedaneum region 430 as the fetus's skull. Furthermore, the ultrasound imaging apparatus 100 may calculate the risk of labor based on at least one of the thickness, area, and volume of the caput succedaneum region 430 and display information indicating the risk of labor such that the user may help the pregnant woman safely deliver the fetus.

Figure 5:
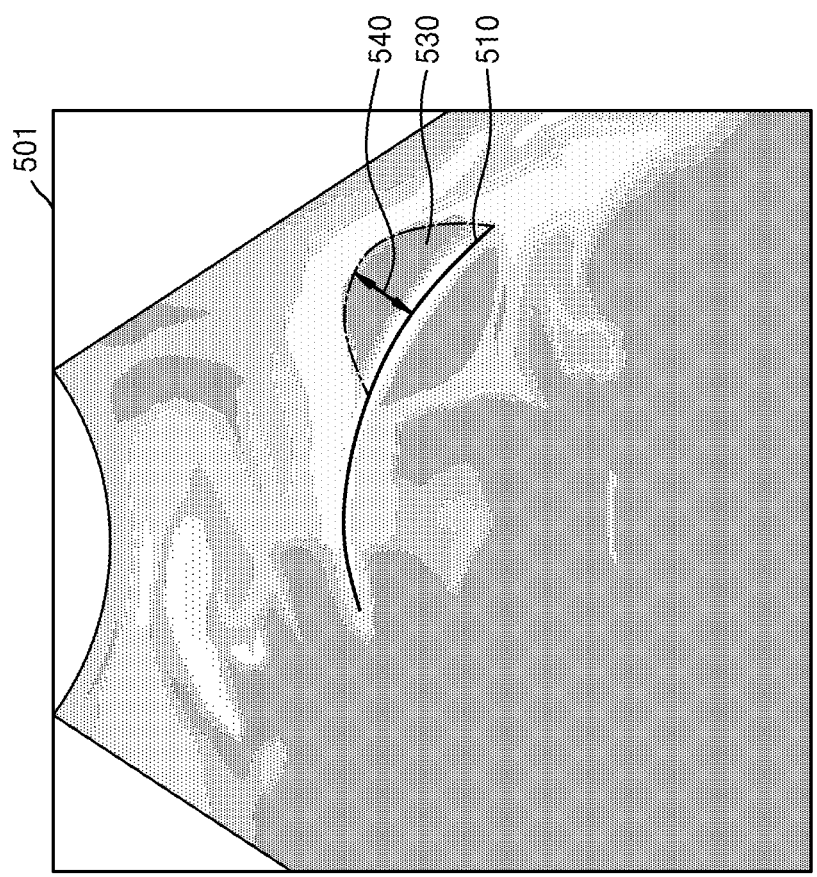
FIG. 5 is an example in which an ultrasound imaging apparatus measures a thickness of caput succedaneum in a fetus, according to an embodiment.
Figure 5:
Figure 5:
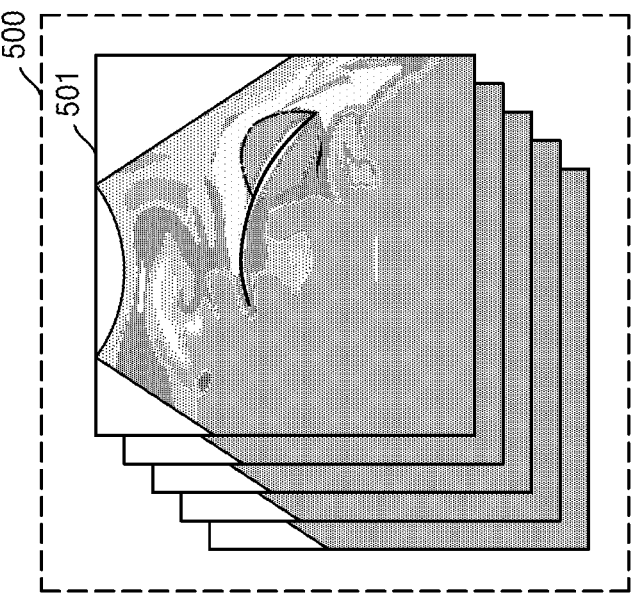

FIG. 5 is an example in which the ultrasound imaging apparatus 100 measures a thickness of caput succedaneum in a fetus, according to an embodiment.

The ultrasound imaging apparatus 100 may measure a thickness of caput succedaneum in a fetus.

According to an embodiment, the processor may measure a thickness of caput succedaneum based on a first normal line that is a longest one among normal lines to a skull 510 that pass through a caput succedaneum region 530. The processor may measure the thickness of the caput succedaneum from a length of the first normal line included in the caput succedaneum region 530. The processor may also control the display 140 to display a marker 540 indicating a region where the thickness of the caput succedaneum region 530 is measured. The marker 540 may be at least a part of the first normal line.

Referring to FIG. 5, the ultrasound imaging apparatus 100 may acquire a plurality of pieces of ultrasound cross-sectional image data based on ultrasound echo signals. For example, the ultrasound imaging apparatus 100 may acquire a plurality of pieces of 2D ultrasound image data via the probe 20. As another example, the ultrasound imaging apparatus 100 may acquire 3D ultrasound image data and acquire 2D ultrasound cross-sectional image data based on the 3D ultrasound image data.

According to an embodiment, the processor may respectively measure thicknesses of caput succedaneum regions in a plurality of ultrasound cross-sectional images 500. The processor may respectively identify skulls in the ultrasound cross-sectional images 500 and measure thicknesses of caput succedaneum regions in the ultrasound cross-sectional images 500 based on first normal lines respectively corresponding to the skulls therein. The processor may also obtain the risk of labor based on a largest thickness among the thicknesses of the caput succedaneum regions in the ultrasound cross-sectional images 500.

According to an embodiment, the processor may measure a thickness of a caput succedaneum region 530 in an ultrasound cross-sectional image 501 showing the skull 510 as being largest from among the ultrasound cross-sectional images 500. In detail, the processor may identify skulls respectively included in the ultrasound cross-sectional images 500 and measure diameters of ellipses respectively corresponding to the skulls. The processor may then identify the ultrasound cross-sectional image 501 showing the largest skull 510 by comparing the diameters of the ellipses with one another. The processor may also obtain the risk of labor based on the thickness of the caput succedaneum region 530 in the ultrasound cross-sectional image 501.

According to an embodiment, the processor may measure a thickness of a caput succedaneum region in an ultrasound cross-sectional image showing a longest mother's pubis (or showing a longest major axis of a cartilage of a pubic symphysis) from among the ultrasound cross-sectional images 500. The processor may identify pubes in the ultrasound cross-sectional images 500 and measure diameters of ellipses respectively corresponding to the pubes. The processor may identify an ultrasound cross-sectional image showing a longest pubis by comparing the diameters of the ellipses with one another. The processor may also obtain the risk of labor based on the thickness of the caput succedaneum region in the ultrasound cross-sectional image showing the longest pubis.

Figure 6:
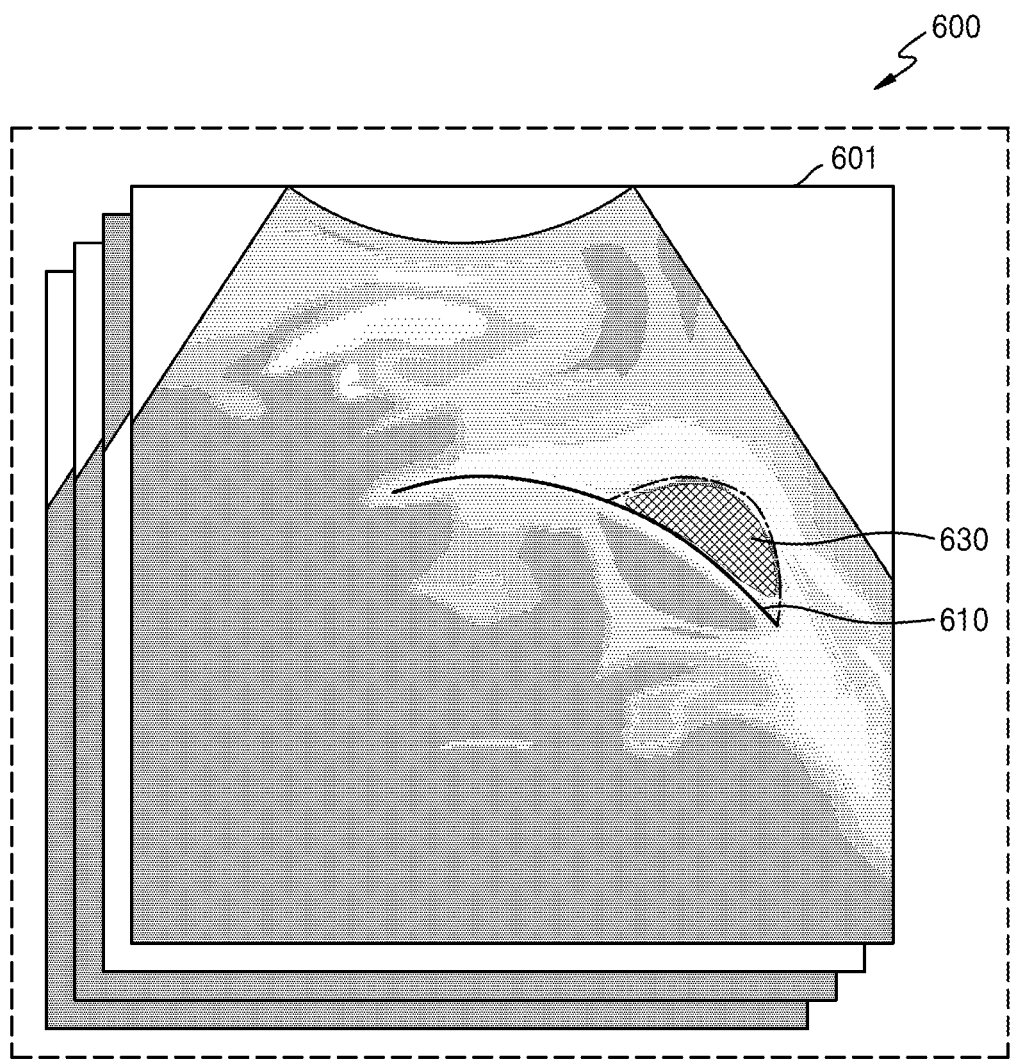
FIG. 6 is an example in which an ultrasound imaging apparatus measures an area and a volume of caput succedaneum in a fetus, according to an embodiment.

FIG. 6 is an example in which the ultrasound imaging apparatus 100 measures an area and a volume of a caput succedaneum in a fetus, according to an embodiment.

The ultrasound imaging apparatus 100 may measure an area of a caput succedaneum region 630 in an ultrasound cross-sectional image 601. The processor may measure an area of the caput succedaneum region 630 based on a proportion of the caput succedaneum region 630 occupying the ultrasound cross-sectional image 601.

According to an embodiment, the processor may measure an area of the caput succedaneum region 630 in the ultrasound cross-sectional image 601 showing the skull 610 as being largest from among a plurality of ultrasound cross-sectional images 600. The processor may also obtain the risk of labor based on the area of the caput succedaneum region 630 in the ultrasound cross-sectional image 601 showing the skull 610 as being largest.

According to an embodiment, the processor may measure an area of a caput succedaneum region in the ultrasound cross-sectional image 601 showing a longest mother's pubis (or showing a longest major axis of a cartilage of a pubic symphysis) from among the ultrasound cross-sectional images 600. The processor may also obtain the risk of labor based on the area of the caput succedaneum region in the ultrasound cross-sectional image showing the longest pubis.

The processor may calculate a volume of a caput succedaneum region based on caput succedaneum regions respectively included in the ultrasound cross-sectional images 600.

According to an embodiment, the processor may measure areas of the caput succedaneum regions respectively included in the ultrasound cross-sectional images 600. The processor may obtain a volume of a caput succedaneum region by stacking the measured areas of the caput succedaneum regions together. The processor may also obtain the risk of labor based on the obtained volume of the caput succedaneum region.

Figure 7:
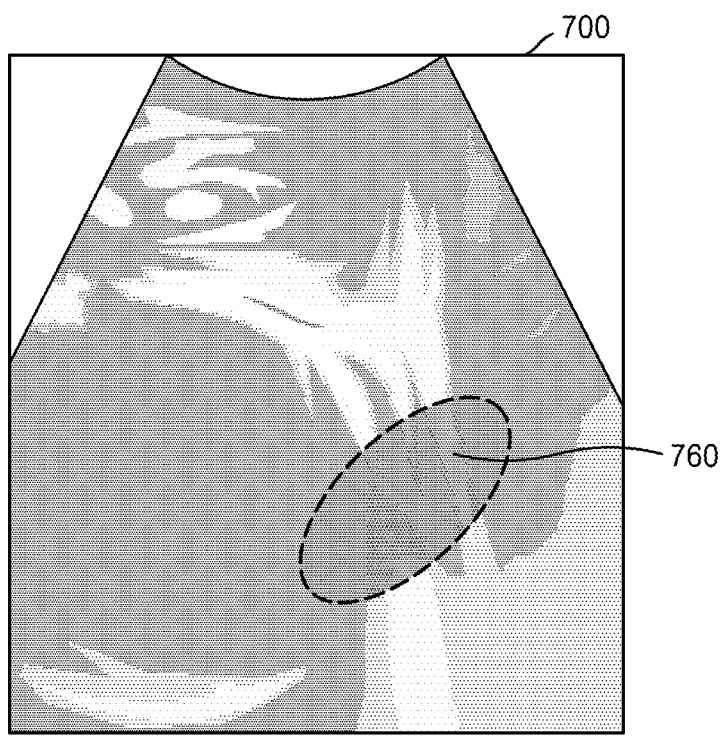
FIG. 7 is an example in which an ultrasound imaging apparatus displays an ultrasound image including a shaded region, according to an embodiment.

FIG. 7 is an example in which the ultrasound imaging apparatus 100 displays an ultrasound image 700 in which a shaded region 760 appears, according to an embodiment.

The ultrasound image 700 may include the shaded region 760. The shaded region 760 may occur due to the loss of an ultrasound echo signal due to a structure that obstructs the passage of an ultrasound signal. Furthermore, the shaded region 760 may occur due to refraction of an ultrasound signal as the ultrasound signal passes through a medium having a different composition and a rounded surface, or attenuation of the refracted ultrasound signal. Furthermore, the shaded region 760 may occur due to refraction of a scan line of an ultrasound signal. The shaded region may also occur due to multiple reflections of an ultrasound signal between a reflector and an ultrasound probe. In addition, the shaded region 760 may appear at lower ends of a fetus's skull and scalp when portions of the fetus's skull and scalp are parallel to the ultrasound probe.

The shaded region 760 in the ultrasound image 700 may include at least a part of a caput succedaneum region. Thus, the presence of the shaded region 760 may prevent the user from accurately identifying the caput succedaneum region. In other words, the user may have difficulties in identifying an outline of the caput succedaneum region due to the presence of the shaded region 760 in the caput succedaneum region. The user may also have difficulties in accurately measuring at least one of a thickness, an area, and a volume of the caput succedaneum region due to the presence of the shaded region 760.

Figure 8:
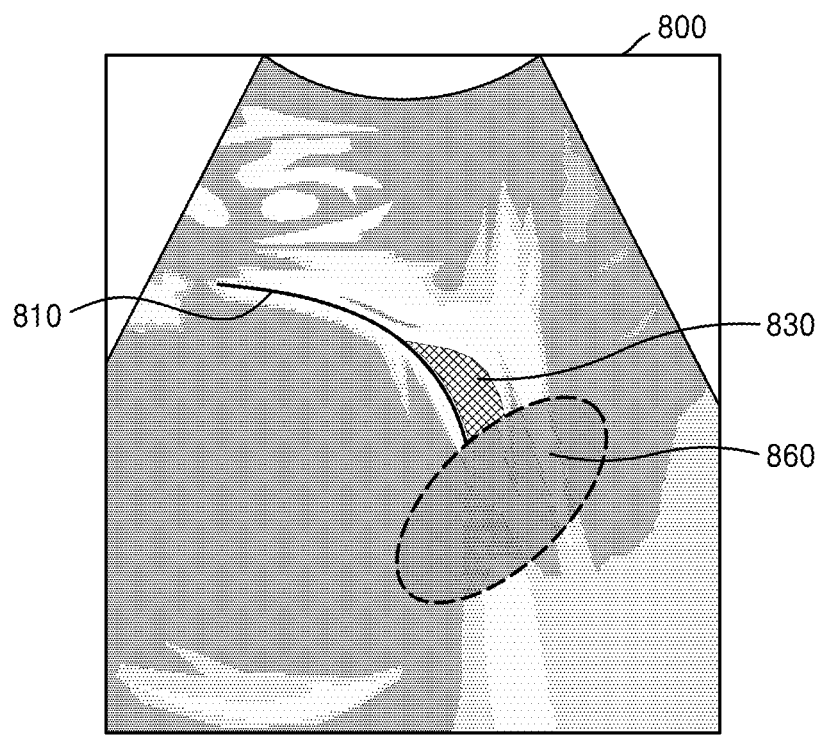
FIG. 8 is an example in which an ultrasound imaging apparatus displays information about a portion of caput succedaneum region excluding a shaded region, according to an embodiment.

FIG. 8 is an example in which the ultrasound imaging apparatus 100 displays information about a caput succedaneum region 830 excluding a shaded region 860, according to an embodiment.

Referring to FIG. 8, even when the shared region 860 is included in an ultrasound image 800, the ultrasound imaging apparatus 100 may identify a fetal skull 810 and the caput succedaneum region 830 from the ultrasound image 800.

Even when the shaded region 860 is present in at least a part of the fetal skull 810, the processor may identify the fetal skull 810.

For example, the processor may identify the fetal skull 810 not overlapped by the shaded region 860 by comparing a region including pixels having high brightness values with the form of at least a part of an ellipse.

As another example, the processor may identify a mother's anatomical structure and then the fetal skull 810 based on a relationship between the mother's anatomical structure and the fetal skull 810. In detail, the processor may identify a mother's pubis and pixels with high brightness values located near the pubis. The processor may identify the fetal skull 810 from pixels that are positioned a predetermined distance from the pubis among the pixels with high brightness values. The processor may also identify the fetal skull 810 from pixels that constitute an elliptical region among the pixels positioned a predetermined distance from the pubis.

Even when the shaded region 860 is present in at least a part of the caput succedaneum region the ultrasound imaging apparatus 100 may identify the caput succedaneum region 830.

For example, the processor may identify the caput succedaneum region 830 based on the identified fetal skull 810. The processor may identify, as the caput succedaneum region 830, pixels having lower brightness values than their neighboring pixels among a plurality of pixels located along a direction of a normal line to the fetal skull 810. The processor may identify, as a region corresponding to a fetal scalp, a region composed of pixels having similar brightness values to pixels in a region corresponding to the fetal skull 810 from among the plurality of pixels located along the direction of the normal line to the fetal skull 810. The processor may also identify a space between the regions respectively corresponding to the fetal skull 810 and the fetal scalp as the caput succedaneum region 830.

The ultrasound imaging apparatus 100 may display information about the caput succedaneum region 830 excluding the shaded region 860.

For example, the ultrasound imaging apparatus 100 may show an outline of the caput succedaneum region 830 excluding the shaded region 860 as a line. Furthermore, the ultrasound imaging apparatus 100 may color-code the caput succedaneum region 830 excluding the shaded region 860 with a predetermined color and display the color-coded caput succedaneum region 830. In this case, the ultrasound imaging apparatus 100 may display a marker (e.g., an indicator) indicating the presence of the shaded region 860 in the ultrasound image 800.

According to an embodiment, the ultrasound imaging apparatus 100 may receive a user input for setting a part of the shaded region 860 as the caput succedaneum region 830. For example, the user may set the caput succedaneum region 830 via the input interface 170 such as a touch screen, a touchpad, a keyboard, a mouse, a trackball, and a jog switch.

The ultrasound imaging apparatus 100 may identify the caput succedaneum region 830 based on the user input. The ultrasound imaging apparatus 100 may display information about the identified caput succedaneum region 830. For example, the ultrasound imaging apparatus 100 may show an outline of the caput succedaneum region 830 as a line. The ultrasound imaging apparatus may also color-code the identified caput succedaneum region 830 with a predetermined color and display the color-coded caput succedaneum region 830. The ultrasound imaging apparatus 100 may also measure at least one of a thickness, an area, and a volume of the identified caput succedaneum region 830 and display a measurement result.

Figure 9:
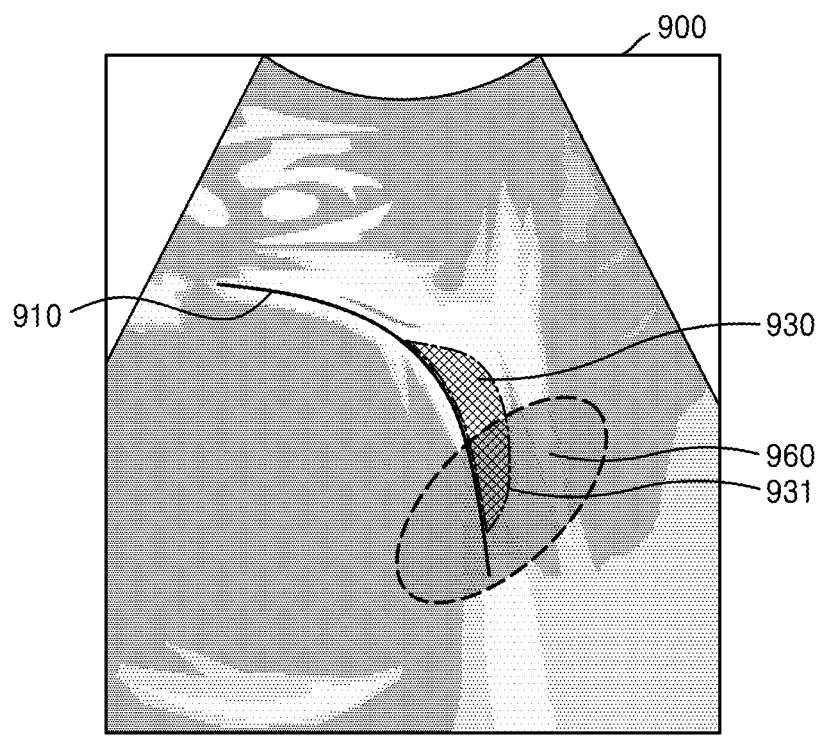
FIG. 9 is an example in which an ultrasound imaging apparatus displays information about a portion of caput succedaneum region included in a shaded region, according to an embodiment.

FIG. 9 is an example in which the ultrasound imaging apparatus 100 displays information about a caput succedaneum region included in a shaded region 960, according to an embodiment;

A part of the caput succedaneum region may not be identified due to the shaded region 960 included in an ultrasound image 900. In other words, the processor may identify a first caput succedaneum region 930 not included in the shaded region 960.

Referring to FIG. 9, the ultrasound imaging apparatus 100 may estimate a second caput succedaneum region 931 included in the shaded region 960.

According to an embodiment, the processor may estimate the second caput succedaneum region 931 based on a shape of the first caput succedaneum region 930. Because formation of caput succedaneum is caused by a pressure placed on a fetal head that passes through a mother's birth canal, caput succedaneum near the birth canal may protrude from beneath a fetal scalp. The processor may also estimate the second caput succedaneum region 931 based on a protruding shape of the first caput succedaneum region 930.

According to an embodiment, the processor may estimate the second caput succedaneum region 931 in the ultrasound image 900 based on a caput succedaneum region identified from a plurality of ultrasound cross-sectional images. The processor may estimate the second caput succedaneum region 931 by comparing the caput succedaneum region identified from the plurality of ultrasound cross-sectional images with the first caput succedaneum region 930 in the ultrasound image 900.

The ultrasound imaging apparatus 100 may display information about the caput succedaneum region based on the first and second caput succedaneum regions 930 and 931. For example, the ultrasound imaging apparatus 100 may set, as the caput succedaneum region, a region obtained by combing the first caput succedaneum region 930 with the second caput succedaneum region 931. The ultrasound imaging apparatus 100 may show as a line an outline of the region obtained by combining the first caput succedaneum region 930 with the second caput succedaneum region 931. The ultrasound imaging apparatus 100 may also color-code with a predetermined color the region obtained by combining the first the first caput succedaneum region 930 with the second caput succedaneum region 931 and display the color-coded region. The ultrasound imaging apparatus 100 may also measure at least one of a thickness, an area, and a volume of the region obtained by combining the first caput succedaneum region 930 with the second caput succedaneum region 931. The ultrasound imaging apparatus 100 may then display a measurement result.

Figure 10:
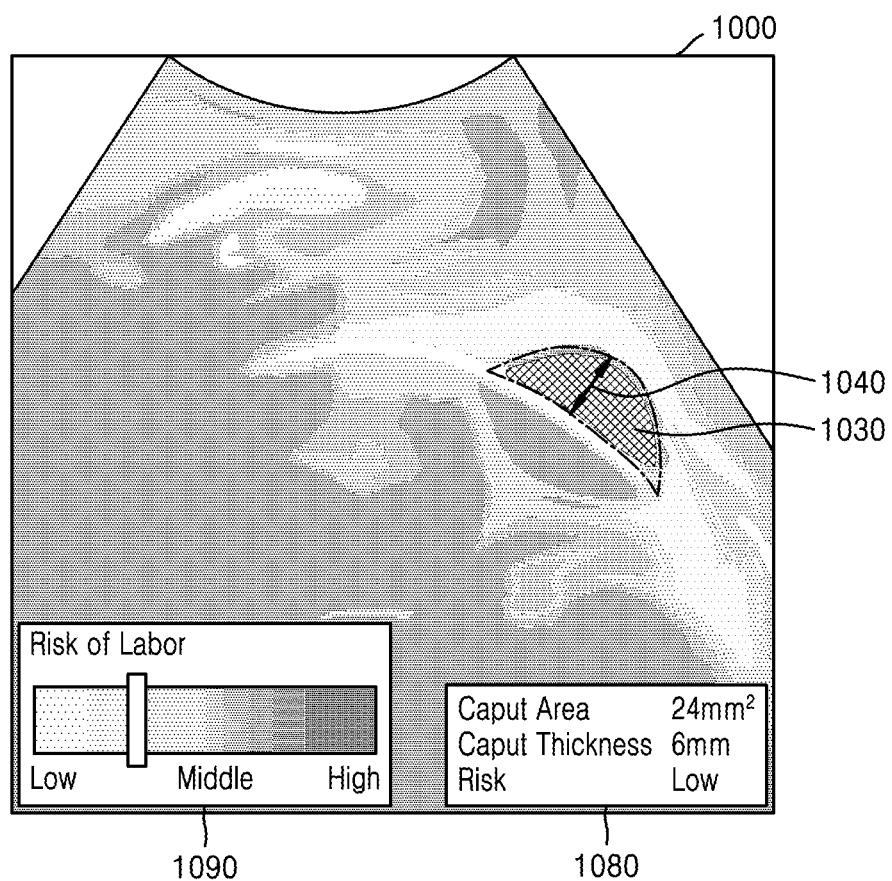
FIG. 10 is an example in which an ultrasound imaging apparatus displays information about the risk of labor obtained based on a caput succedaneum region, according to an embodiment.
Figure 11:
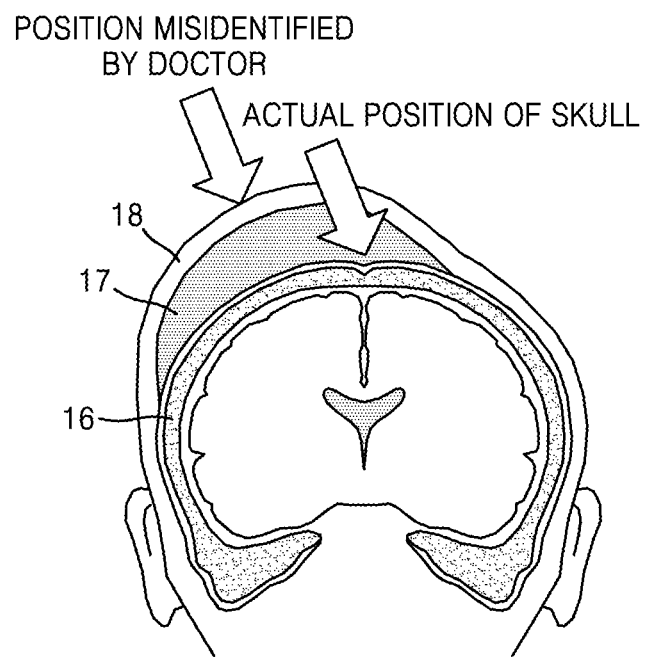
FIG. 11 illustrates an example in which a doctor misidentifies the position of the skull of a fetus due to caput succedaneum in the fetus.
Figure 12A:
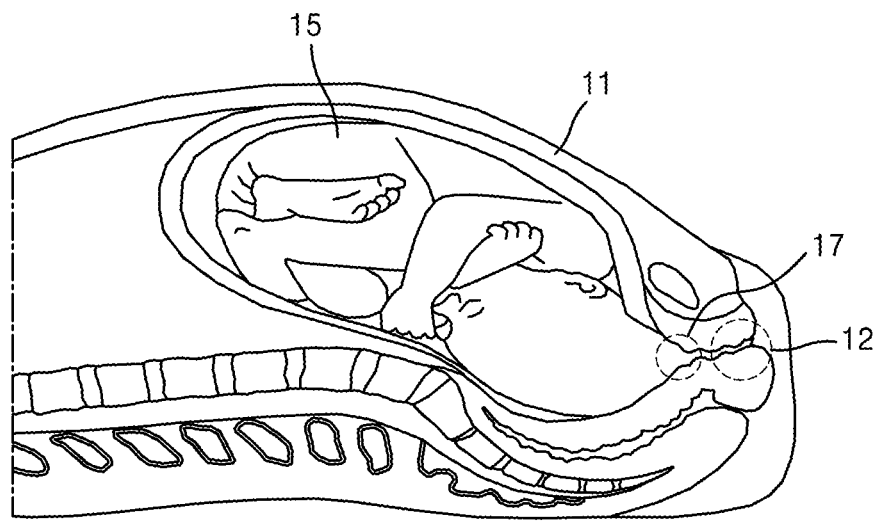
FIGS. 12A and 12B illustrate the occurrence of caput succedaneum as a fetus passes through a birth canal.
Figure 12B:
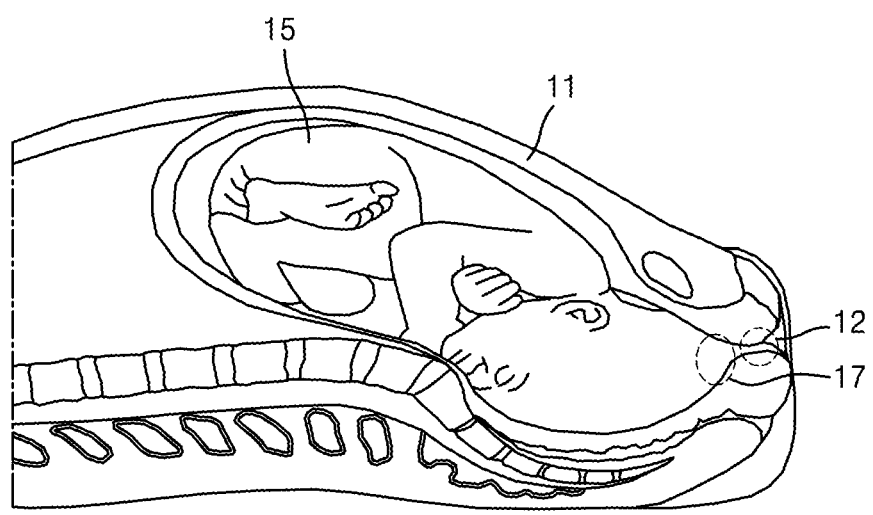

FIG. 10 is an example in which the ultrasound imaging apparatus 100 displays information about the risk of labor obtained based on a caput succedaneum region, according to an embodiment.

Referring to FIG. 10, the ultrasound imaging apparatus 100 may obtain the risk of labor. The risk of labor refers to the possibility of causing a physical injury to a pregnant woman or fetus during a labor process. For example, when a fetus cannot easily pass through a birth canal due to pressure in the birth canal, the fetus or pregnant woman may suffer a physical injury. Thus, the ultrasound imaging apparatus 100 may obtain and display the risk of labor before a physical damage occurs to the fetus or pregnant woman, thereby allowing the user to prepare a safe labor plan.

Because caput succedaneum occurs in the fetus due to pressure in the birth canal, the risk of labor may increase as the caput succedaneum increases in size. Thus, the ultrasound imaging apparatus 100 may obtain the risk of labor based on a size of the caput succedaneum in the fetus. The size of the caput succedaneum may be derived from at least one of a thickness, an area, and a volume of a caput succedaneum region.

According to an embodiment, the ultrasound imaging apparatus 100 may obtain the risk of labor based on a thickness of a caput succedaneum region 1030. In detail, the processor may determine the risk of labor by comparing the thickness of the caput succedaneum region 1030 with a preset threshold.

For example, a preset first threshold may be 9 mm, and a preset second threshold may be 12 mm. In this case, the preset threshold may be set based on a first stage of labor. In other words, the processor may obtain the risk of labor by comparing either the first or second preset threshold with a thickness of caput succedaneum in the fetus that is measured over a period from the time when the pregnant woman's uterus contracts at regular intervals until the time when a cervix opens completely.

When the thickness of the caput succedaneum region 1030 is less than 9 mm, the processor may identify the risk of labor as being 'low' or 'safe'. When the thickness of the caput succedaneum region 1030 is greater than or equal to 9 mm but less than 12 mm, the processor may identify the risk of labor as being 'normal'. When the thickness of the caput succedaneum region 1030 is greater than or equal to 12 mm, the processor may identify the risk of labor as being 'high' or 'dangerous'.

According to an embodiment, the ultrasound imaging apparatus 100 may display the obtained risk of labor in at least a part of an ultrasound image 1000. For example, the ultrasound imaging apparatus 100 may display at least one category from among symbols, letters, numbers, and colors that represent at least one of pieces of information about a thickness, an area, and a volume of the caput succedaneum region 1030 as well as the risk of labor obtained based on the at least one of the pieces of information.

Referring to FIG. 10, for example, the ultrasound imaging apparatus 100 may display, in a region of the ultrasound image 1000, information 1080 composed of letters and numbers indicating a thickness and an area of the caput succedaneum region 1030 and the risk of labor obtained based on the thickness and the area thereof.

Furthermore, the ultrasound imaging apparatus 100 may display information about the caput succedaneum region 1030, together with information about the risk of labor. For example, the ultrasound imaging apparatus 100 may display a marker 1040 indicating a region where the thickness of the caput succedaneum region 1030 is measured, together with the information 1080 indicating the risk of labor obtained based on the thickness of the caput succedaneum region 1030.

According to an embodiment, the processor may color-code the caput succedaneum region 1030 with a color corresponding to the obtained risk of labor. For example, when the risk of labor is identified as being 'low' or 'safe', the processor may color-code the caput succedaneum region 1030 with green. Furthermore, when the risk of labor is identified as being 'normal', the processor may color-code the caput succedaneum region 1030 with yellow. In addition, when the risk of labor is identified as being 'high' or 'dangerous', the processor may color-code the caput succedaneum region 1030 with red.

The ultrasound imaging apparatus 100 may display the color-coded caput succedaneum region 1030. The ultrasound imaging apparatus 100 may display a graph 1090 related to a color representing the risk of labor. The ultrasound imaging apparatus 100 may also display on the graph 1090 a marker corresponding to the color used to color-code the caput succedaneum region 1030. The user may easily identify the risk of labor from the color-coded caput succedaneum region 1030 and the graph 1090.

Embodiments may be implemented through non-transitory computer-readable recording media having stored therein computer-executable instructions and data. The instructions may be stored in the form of program codes, and when executed by at least one processor, generate a predetermined program module to perform a specific operation. Furthermore, when being executed by the processor, the instructions may perform specific operations according to the embodiments.

What is claimed is:

1. A method of generating an ultrasound image, performed by an ultrasound imaging apparatus, the method comprising:
    transmitting ultrasound signals to an object;
    receiving ultrasound echo signals from the object;
    generating a plurality of ultrasound cross-sectional images each including a fetus based on the received ultrasound echo signals;
    identifying the fetus's skull from each of the plurality of ultrasound cross-sectional images;
    selecting an ultrasound cross-sectional image showing the fetus's skull as being largest from among the plurality of ultrasound cross-sectional images;
    identifying a caput succedaneum region corresponding to caput succedaneum occurring in the fetus from the selected ultrasound cross-sectional image; and
    displaying information about the caput succedaneum region.

2. The method of claim 1, wherein the caput succedaneum region comprises a pixel with a lower brightness value than its neighboring pixels from among a plurality of pixels located along a direction of a normal line to the identified fetus's skull.

3. The method of claim 1, wherein the identifying of the caput succedaneum region comprises:
    identifying a scalp of the fetus, the fetus's scalp being located in the vicinity of the identified fetus's skull; and
    identifying a region between the fetus's skull and the fetus's scalp as the caput succedaneum region.

4. The method of claim 1, further comprising
    measuring a thickness of the caput succedaneum region based on a normal line that is a longest one among normal lines to the fetus's skull that pass through the caput succedaneum region,
    wherein the displaying of the information about the caput succedaneum region comprises displaying the measured thickness of the caput succedaneum region.

5. The method of claim 1, wherein the identifying of the caput succedaneum region comprises identifying a shaded region including at least a portion of the caput succedaneum region, and
    wherein the displaying of the information about the caput succedaneum region comprises displaying information about a portion of the caput succedaneum region excluding the shaded region.

6. The method of claim 5, wherein the identifying of the caput succedaneum region comprises estimating the at least a portion of the caput succedaneum region included in the shaded region, and
    wherein the displaying of the information about the caput succedaneum region comprises displaying information about the estimated at least a portion of the caput succedaneum region.

7. The method of claim 1, further comprising:
    receiving a user input of adjusting the caput succedaneum region;
    re-identifying the caput succedaneum region based on the user input; and
    displaying information about the re-identified caput succedaneum region.

8. The method of claim 1, further comprising:
    measuring a thickness of the caput succedaneum region;
    obtaining a risk of labor in a pregnant woman by comparing the measured thickness of the caput succedaneum region with a preset threshold; and
    displaying information about the risk of labor.

9. The method of claim 8, wherein the displaying of the information about the risk of labor comprises:
- color-coding the caput succedaneum region with a color corresponding to a result of comparing the thickness of the caput succedaneum region with the threshold; and
- displaying the color-coded caput succedaneum region.

10. An ultrasound imaging apparatus comprising:
- an ultrasound probe configured to transmit ultrasound signals to an object and receive ultrasound echo signals from the object;
- a processor configured to generate a plurality of ultrasound cross-sectional images each including a fetus based on the received ultrasound echo signals, identify the fetus's skull from each of the plurality of ultrasound cross-sectional images, select an ultrasound cross-sectional image showing the fetus's skull as being largest from among the plurality of ultrasound cross-sectional images, and identify a caput succedaneum region corresponding to caput succedaneum occurring in the fetus from the selected ultrasound cross-sectional image; and
- a display displaying information about the caput succedaneum region.

11. The ultrasound imaging apparatus of claim 10, wherein the caput succedaneum region comprises a pixel with a lower brightness value than its neighboring pixels from among a plurality of pixels located along a direction of a normal line to the identified fetus's skull.

12. The ultrasound imaging apparatus of claim 10, wherein the processor is further configured to:
- identify a scalp of the fetus, the fetus's scalp being located in the vicinity of the identified fetus's skull; and
- identify a region between the fetus's skull and the fetus's scalp as the caput succedaneum region.

13. The ultrasound imaging apparatus of claim 10, wherein the processor is further configured to
- measure a thickness of the caput succedaneum region based on a normal line that is a longest one among normal lines to the fetus's skull that pass through the caput succedaneum region, and
- wherein the display further displays the measured thickness of the caput succedaneum region.

14. The ultrasound imaging apparatus of claim 10, wherein the processor is further configured to:
- measure areas of caput succedaneum regions respectively included in the plurality of ultrasound cross-sectional images; and
- calculate a volume of the caput succedaneum region by stacking the measured areas of the caput succedaneum regions, and
- wherein the display further displays the measured volume of the caput succedaneum region.

15. The ultrasound imaging apparatus of claim 10, wherein the processor is further configured to identify a shaded region including at least a portion of the caput succedaneum region, and
- wherein the display further displays information about a portion of the caput succedaneum region excluding the shaded region.

16. The ultrasound imaging apparatus of claim 15, wherein the processor is further configured to estimate the at least a portion of the caput succedaneum region included in the shaded region, and
- wherein the display further displays information about the estimated at least a portion of the caput succedaneum region.

17. The ultrasound imaging apparatus of claim 10, further comprising a user input interface configured to receive a user input of adjusting the caput succedaneum region,
- wherein the processor is further configured to re-identify the caput succedaneum region based on the user input, and
- wherein the display further displays information about the re-identified caput succedaneum region.

18. The ultrasound imaging apparatus of claim 10, wherein the processor is further configured to:
- measure a thickness of the caput succedaneum region; and
- obtain a risk of labor in a pregnant woman by comparing the measured thickness of the caput succedaneum region with a preset threshold,
- wherein the display further displays information about the risk of labor.

19. The ultrasound imaging apparatus of claim 18, wherein the processor is further configured to color-code the caput succedaneum region with a color corresponding to a result of comparing the thickness of the caput succedaneum region with the threshold, and
- wherein the display further displays the color-coded caput succedaneum region.

20. A method of generating an ultrasound image, performed by an ultrasound imaging apparatus, the method comprising:
- transmitting ultrasound signals to an object;
- receiving ultrasound echo signals from the object;
- generating a plurality of ultrasound cross-sectional images each including a fetus based on the received ultrasound echo signals;
- identifying the fetus's skull from each of the plurality of ultrasound cross-sectional images;
- measuring areas of caput succedaneum regions respectively included in the plurality of ultrasound cross-sectional images;
- calculating a volume of the caput succedaneum region by stacking the measured areas of the caput succedaneum regions; and
- displaying information about the caput succedaneum region,
- wherein the displaying of the information about the caput succedaneum region comprises displaying the measured volume of the caput succedaneum region.

* * * * *